United States Patent [19]

Wirth et al.

[11] Patent Number: 4,737,300
[45] Date of Patent: Apr. 12, 1988

[54] ADDITIVES FOR MATERIALS

[75] Inventors: Hermann O. Wirth, Bensheim; Hans-Helmut Friedrich, Lautertal, both of Fed. Rep. of Germany

[73] Assignee: Ciba-Geigy Corporation, Ardsley, N.Y.

[21] Appl. No.: 733,180

[22] Filed: May 10, 1985

[30] Foreign Application Priority Data

May 15, 1984 [CH] Switzerland ......................... 2388/84

[51] Int. Cl.$^4$ ................ C10M 133/00; C10M 135/00
[52] U.S. Cl. .................................... 252/41; 252/42.1;
    252/46.3; 252/46.4; 252/47.5; 252/48.2;
    252/48.6; 568/46; 568/48; 549/39; 564/154;
    564/162; 564/201; 560/15; 560/17; 560/152;
    560/153; 562/426; 562/431; 562/556; 562/581
[58] Field of Search ............. 252/47.5, 48.2, 48.6,
    252/46.3, 46.4, 41, 42.1; 568/48, 46; 549/39;
    564/154, 162, 201; 560/15, 17, 152, 153, 154;
    562/426, 431, 556, 581

[56] References Cited

U.S. PATENT DOCUMENTS

| | | | |
|---|---|---|---|
| 2,559,510 | 7/1951 | Mikeska et al. | 252/48.6 |
| 3,376,322 | 4/1968 | Thompson | 252/47.5 |
| 3,494,963 | 2/1970 | Andersen | 252/48.2 |
| 3,630,900 | 12/1971 | van der Voort | 252/48.2 |
| 4,178,253 | 12/1979 | Lee et al. | 252/47.5 |
| 4,189,587 | 2/1980 | Holt et al. | 252/47.5 |
| 4,250,046 | 2/1981 | Przybylinski | 252/48.2 |
| 4,384,967 | 5/1983 | Salentine et al. | 252/48.2 |

FOREIGN PATENT DOCUMENTS 3854 2/1966 France .
701993 1/1954 United Kingdom ............... 252/48.6

Primary Examiner—William R. Dixon, Jr.
Assistant Examiner—Cynthia A. Prezlock
Attorney, Agent, or Firm—Edward McC. Roberts; Harry Falber

[57] ABSTRACT

The invention relates to material containing aldosemarcaptals of the formula I

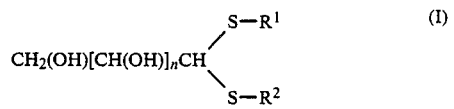

wherein n can be an integer from 2 to 6, and wherein $R^1$ and $R^2$ are identical or different, and in each case are $C_1$-$C_{18}$-alkyl, which is unsubstituted, substituted or interrupted by —O— or —S—, or are —($CH_2$)$_r$—CO—N($C_1$-$C_{17}$-alkyl)$_2$, r being 1 or 2, or are phenyl, benzyl or —($CH_2$)$_r$—CO—O—$R^3$, in which r can be 1 or 2 and $R^3$ is an alkali metal or $C_1$-$C_{14}$-alkyl; also wherein $R^1$ and $R^2$ are —$CH_2$—CH(OH)—$R^4$, in which $R^4$ is hydrogen, or $C_1$-$C_{16}$-alkyl, unsubstituted or substituted by —OH, or —$CH_2$—Y—($C_1$-$C_{15}$-alkyl), in which Y is —O— or —S—; or wherein $R^1$ and $R^2$ together form —($CH_2$)$_m$—, in which m can be an integer from 2 to 4; to the use of the aldosemercaptals in lubricants and hydraulic fluids which can be based on oil or water or mixtures thereof, or in plastics; and to some novel aldosemercaptals.

7 Claims, No Drawings

ADDITIVES FOR MATERIALS

The invention relates to material containing aldosemercaptals, to the use of these aldosemercaptals as additives in plastics or lubricants, or in hydraulic fluids based on oil or water or on mixtures thereof, and to novel aldosemercaptals.

Some aldosemercaptals and the production thereof are known from the literature, for example from Chem. Ber. 27, 673 (1894) or from Chem. Ber. 84, 780 (1951); these served to effect identification and isolation of aldoses. The application of specific representatives is described for special fields in U.S. Pat. Nos. 3,635,717 and 3,635,736; on the one hand they are used there to provide an improved light-sensitive, photographic silver halide emulsion, and on the other hand they are used as flavouring agents in foodstuffs.

In order to improve the performance characteristics of lubricants and to counteract their natural or technically conditioned ageing phenomena, additives are incorporated into the lubricants. Oxidation reactions in a lubricant occurring at elevated temperature to a greater extent as a result of atmospheric oxygen can for example be inhibited by the addition of antioxidants. Detergents are used for example because inter alia in motor oils they keep oil-insoluble oxidation and combustion residues in suspension, and thus prevent deposits occurring on metal surfaces and sludge forming in the motor, as well as preventing wear as a result of neutralisation of acid combustion products. With high pressures between the contact faces, for example of gear wheels or cam follower systems, the lubricant moreover has to prevent galling on the metal surfaces: this prevention is ensured for example by the use of so-called high-pressure and anti-wear additives.

When on the other hand oxygen and moisture for example simultaneously act on a metal surface, corrosion can occur, and it is for this reason that corrosion inhibitors are used to prevent these substances having access to the metal surface. In order to prevent for example oil losses due to dripping off or spattering, so-called adhesion promoters are employed. It is known that certain substances, used as additives for lubricants, combine a number of such properties, and it is because of this that they are designated as so-called multipurpose additives. Such substances are—as can easily be imagined—naturally in great demand for economic and practical reasons.

When PVC is thermally stressed, for example in the case of thermoplastic deformation, there can occur damage as a result of cleavage of hydrogen chloride (dehydrochlorination), autooxidation and mechanochemical fragmentation. To avoid as far as possible damaging PVC during processing and to retain its performance characteristics, there are added specific stabilisers which both retard dehydrochlorination and autooxidation (preventive stabiliser functions) and counteract, at least partially, damage that has already occurred (curative stabiliser functions).

It is known that natural and synthetic polymers are subject to oxidation as a result of oxygen; this can take effect in an undesirable manner during the whole of the service life of a polymer. The ageing phenoena associated therewith are on the one hand of a visual nature, and on the other hand there occurs, more or less parallel therewith, a deterioration in mechanical properties. In the case of the antioxidants to be incorporated into the polymers, they are chemical compounds which can retard the oxidation of a polymer and the ageing phenomena resulting therefrom.

Since most plastics by virtue of their chemical constitution are outstanding insulators, they are used for example also as materials in high-frequency electrical engineering. A disadvantage in this respect is that charges when once applied cannot be conducted away rapidly enough on account of the low surface conductivity, a factor which leads to the build up of high electrical charges. The surface conductivity can be improved by the use of antistatic agents, so that the charges can be conducted away across the surface.

The present invention relates to material containing a compound of the formula I

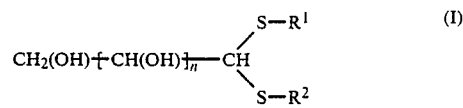

wherein n can be an integer from 2 to 6, and wherein $R^1$ and $R^2$ are identical or different, and in each case are $C_1$–$C_{18}$-alkyl, which is unsubstituted, substituted or interrupted by —O— or —S—, or are —($CH_2$)$_r$—CO—N($C_1$-$C_{17}$-alkyl)$_2$, r being 1 or 2, or are phenyl, benzyl or —($CH_2$)$_r$—CO—O—$R^3$, in which r can be 1 or 2 and $R^3$ is an alkali metal or $C_1$-$C_{14}$-alkyl; also wherein $R^1$ and $R^2$ are —$CH_2$—CH(OH)—$R^4$, in which $R^4$ is hydrogen, or $C_1$-$C_{16}$-alkyl, unsubstituted or substituted by —OH, or —$CH_2$—Y—($C_1$-$C_{15}$-alkyl), in which Y is —O— or —S—; or wherein $R^1$ and $R^2$ together form —($CH_2$)$_m$—, in which m can be an integer from 2 to 4.

The aformentioned material can be organic material or water or mixtures thereof, preferably however organic material.

When $R^1$ and/or $R^2$ are $C_1$-$C_{18}$-alkyl, they are straight-chain or branched-chain substituents, for example: methyl, ethyl, n-propyl, isopropyl, n-butyl, sec-butyl, tert-butyl, pentyl, hexyl, heptyl, octyl, nonyl, decyl, undecyl, dodecyl, tridecyl, tetradecyl, pentadecyl, hexadecyl, heptadecyl or octadecyl, especially however straight-chain or branched-chain octyl, nonyl, decyl, undecyl, dodecyl, pentadecyl or hexadecyl, and in particular 2-ethyl-hexyl, 2-butyl-octyl or 2-hexyl-decyl, as well as isoprenoid decyl or pentadecyl.

In the case of $C_1$-$C_{17}$-alkyl and $C_1$-$C_{15}$-alkyl, they are straight-chain and branched-chain substituents, for example methyl, ethyl, n-propyl, isopropyl, n-butyl, sec-butyl, tert-butyl, pentyl, hexyl, heptyl, octyl, nonyl, decyl, undecyl, dodecyl, tridecyl, tetradecyl, pentadecyl, hexadecyl or heptadecyl. Hexadecyl and heptadecyl are not included in $C_1$-$C_{15}$-alkyl When $R^3$ in —($CH_2$)$_r$—CO—O—$R^3$, which can function as substituent for $R^1$ and/or $R^2$, is an alkali metal it is lithium, sodium or potassium, particularly sodium or potassium; and when $R^3$ is $C_1$-$C_{14}$-alkyl, the substituents are straight-chain or branched-chain, for example: methyl ethyl, n-propyl, isopropyl, n-butyl, sec-butyl, tert-butyl, pentyl, hexyl, heptyl, octyl, nonyl, decyl, undecyl, dodecyl tridecyl or tetradecyl.

When $R^4$ in —$CH_2$—CH(OH)—$R^4$, which can function as a substituent for $R^1$ and/or $R^2$, is $C_1$-$C_{16}$-alkyl, the substituents are straight-chain or branched-chain, for example: methyl, ethyl, n-propyl, isopropyl, n-butyl, sec-butyl, tert-butyl, pentyl, hexyl, heptyl, octyl, tertnonyl, decyl, undecyl, tert-dodecyl, tridecyl, tetradecyl, pentadecyl or hexadecyl. If $C_1$-$C_{16}$-alkyl denoted by $R^4$ is substituted by —OH, all monohydroxy-position isomers are possible; there can however occur polysubstitutions by —OH, preferably disubstitutions.

If $R^1$ and $R^2$ together, as —$(CH_2)_m$; form with the S atoms to which they are bound a heterocyclic ring, it is for example a ring having 5 to 7 ring atoms, preferably a ring having 5 or 6 ring atoms.

Preferred organic material is that containing a compound of the formula I wherein n can be an integer from 3 to 6, and wherein $R^1$ and $R^2$ are identical and are $C_1$-$C_{16}$-alkyl, which is unsubstituted or interrupted by —O— or —S—, or are phenyl, benzyl or —$(CH_2)_r$—CO—O—$R^3$, in which r can be 1 or 2 and $R^3$ is an alkali metal; or wherein $R^1$ and $R^2$ are —$CH_2$—CH(OH)—$R^4$, in which $R^4$ is hydrogen or $C_1$-$C_{14}$-alkyl or $CH_2$—O—($C_1$-$C_{13}$-alkyl); or wherein $R^1$ and $R^2$ together form —$(CH_2)_m$, in which m can be an integer from 2 to 4.

Particularly preferred organic material is that containing a compound of the formula I wherein n can be an integer from 3 to 6, and wherein $R^1$ and $R^2$ are identical and are $C_8$-$C_{16}$-alkyl or —$CH_2$—O—($C_7$-$C_{15}$-alkyl), phenyl, benzyl or —$CH_2$—COOK, —$CH_2$—COONa or —$CH_2$—$CH_2$—COOK; or wherein $R^1$ and $R^2$ are —$CH_2$—CH(OH)—$R_4$, in which $R^4$ is hydrogen or $C_6$-$C_{14}$-alkyl or —$CH_2$—O—($C_5$-$C_{13}$-alkyl); or wherein $R^1$ and $R^2$ together form —$(CH_2)_m$, in which m can be an integer from 2 to 4.

Further subject matter of the present invention are compounds of the formula I wherein n can be an integer from 2 to 6, and wherein $R^1$ and $R^2$ are identical or different, and in each case are branched $C_5$-$C_{18}$-alkyl, —$(CH_2)_r$—CO—O—$R^3$, in which r can be 1 or 2 and $R^3$ is an alkali metal or $C_1$-$C_{14}$-alkyl, or are —$CH_2$—CH(OH)—$R^4$, in which $R^4$ is hydrogen, or $C_1$-$C_{16}$-alkyl, unsubstituted or substituted by —OH, or is —$CH_2$—Y—($C_1$-$C_{15}$-alkyl), in which Y is —O— or —S—, especially however R' and $R^2$ are —$(CH_2)_r$—CO—$OR^3$ or —$CH_2$—CH(OH)—$R^4$.

Preferred compounds of the formula I are those wherein n is an integer from 3 to 6, and wherein $R^1$ and $R^2$ are identical, and are —$CH_2$—CH—[$(CH_2)_q$—$CH_3$][$CH_2)_{q+2}$—$CH_3$], in which q can be 1 to 5, or are —$(CH_2)_r$—CO—O—$R^3$, in which r can be 1 or 2 and $R^3$ is an alkali metal, or are —$CH_2$—CH(OH)—$R^4$, in which $R^4$ is hydrogen or $C_1$-$C_{14}$-alkyl or —$CH_2$—O—($C_1$-$C_{13}$-alkyl).

Particularly preferred compounds of the formula I are those wherein n can be an integer from 4 to 6, and wherein $R^1$ and $R^2$ are identical and are -2-ethyl-hexyl, -2-butyloctyl, 2hexyl-decyl, —$CH_2$—COOK, —$CH_2$—COONa or —$CH_2$—$CH_2$—COOK; or wherein $R^1$ and $R^2$ are —$CH_2$—CH(OH)—$R^4$, in which $R^4$ is hydrogen, or $C_6$-$C_{14}$-alkyl or —$CH_2$—O—($C_5$-$C_{13}$-alkyl).

The interpretation already given by way of example for $R^3$ and $R^4$ is to apply here also for the novel aldosemercaptals of the formula I.

The following are given as examples of the novel compounds of the formula I:

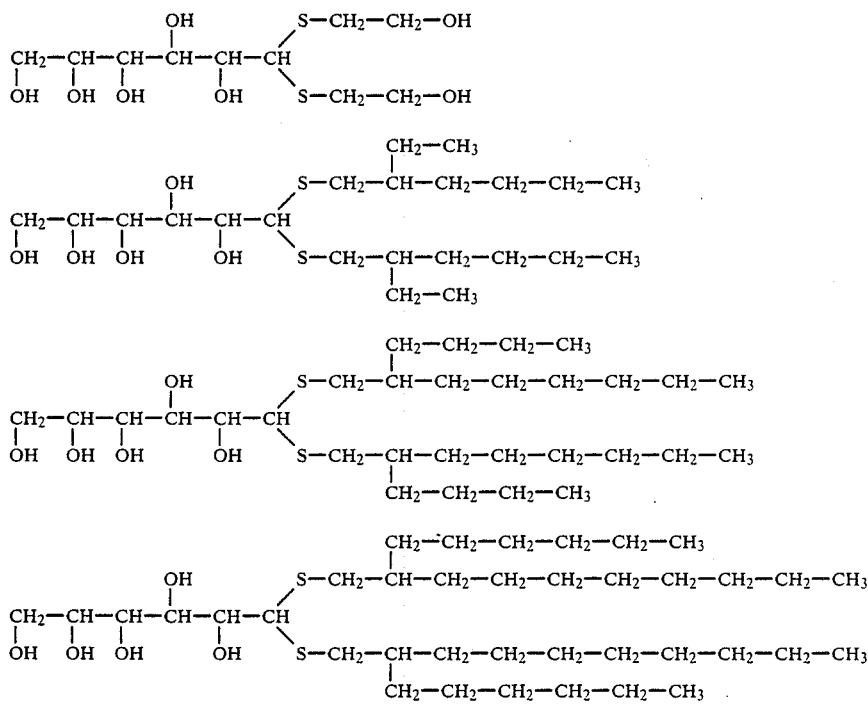

The known and novel aldosemercaptals of the formula I are produced by method known per se. Methods of synthesis are described, inter alia, in Chem. Ber. 27, 673 (1984), J.A.C.S. 53, 4 379 (1931), Chem. Ber. 49, 2056 (1916) or Chem. Ber. 84, 780 (1951).

The use of an ion exchange resin in the H form is particularly advantageous for the synthesis of aldosemercaptals.

The aldosemercaptals of the formula I are suitable as additives for a series of substrates. In this instance, howver, consideration is to be given specifically to their use in lubricants, hydraulic fluids and plastics.

To the lubricant are added 0.001-5.0% by weight, preferably however 0.005-3.0% by weight, and particularly preferably 0.1-1.0% by weight, of the aldosemercaptal of the formula I, relative to the weight of the lubricant formulation.

When mineral and synthetic lubricating oils, hydraulic fluids and lubricating greases are treated in the manner described, they acquire excellent properties, the increase in lubricating efficiency being reflected in the greatly reduced level of wear on the parts being lubricated. The increased effectiveness is to be attributed to the fact that the aldosemercaptals of the formula I intensify, as multipurpose additives, the antioxidising, anticorrosive and dispersing action of the lubricants; they improve above all the high-pressure behaviour and anti-wear activity and, as adhesion promoters, they prevent oil losses.

The lubricants concerned are familiar to a person skilled in the art, and are described for example in the "Schmiermittel-Taschenbuch" [Lubricant Handbook] (Hüthig Verlag (Publishers), Heidelberg, 1974). Particularly suitable lubricants, besides mineral oils, are for example poly-α-olefins, lubricants based on esters; phosphates, glycols, polyglycols and polyalkylene glycols.

The lubricant formulations can additionally contain other additives, which are added in order to improve further performance characteristics, for example: antioxidants, metal passivators, rust inhibitors, viscosity-index improvers, pour-point depressors, dispersants/-surfactants and anti-wear additives. Examples to be mentioned are:

Examples of phenolic antioxidants

1. Alkylated monophenols
2,6-di-tert-butyl-4-methylphenol,
2,6-di-tert-butylphenol,
2-tert-butyl-4,6-dimethylphenol,
2,6-di-tert-butyl-4-ethylphenol,
2,6-di-tert-butyl-4-ethylphenol,
2,6-di-tert-butyl-4-n-butylphenol,
2,6-di-tert-butyl-4-i-butylphenol,
2,6-di-cyclopentyl-4-methylphenol,
2-(α-methylcyclohexyl)-4,6-dimethylphenol,
2,6-di-octadecyl-4-methylphenol,
2,4,6-tri-cyclohexylphenol,
2,6-di-tert-butyl-4-methoxymethylphenyl, and o-tert-butylphenol.

2. Alkylated hydroquinones
2,6-di-tert-butyl-4-methoxyphenol,
2,5-di-tert-butyl-hydroquinone,
2,5-di-tert-amyl-hydroquinone, and
2,6-diphenyl-4-octadecyloxyphenol.

3. Hydroxylated thiodiphenyl ethers
2,2'-thio-bis(6-tert-butyl-4-methylphenol),
2,2'-thio-bis(4-octylphenol),
4,4'-thio-bis(6-tert-butyl-3-methylphenol), and
4,4'-thio-bis(6-tert-butyl-2-methylphenol).

4. Alkylidene bisphenols
2,2'-methylene-bis(6-tert-butyl-4-methylphenol),
2,2'-methylene-bis(6-tert-butyl-4-ethylphenol),
2,2'-methylene-bis[4-methyl-6-(α-methylcyclohexyl)phenol],
2,2'-methylene-bis(4-methyl-6-cyclohexylphenol),
2,2'-methylene-bis(6-nonyl-4-methylphenol),
2,2'-methylene-bis(4,6-di-tert-butylphenol),
2,2'-ethylidene-bis(4,6-di-tert-butylphenol),
2,2'-ethylidene-bis(6-tert-butyl-4-isobutylphenol),
2,2'-methylene-bis[6-(α-methylbenzyl)-4-nonylphenol],
2,2'-methylene-bis[6-(α,α-dimethylbenzyl)-4-nonylphenyl],
4,4'-methylene-bis(2,6-di-tert-butylphenol),
4,4'-methylene-bis(6-tert-butyl-2-methylphenol),
1,1-bis(5-tert-butyl-4-hydroxy-2-methylphenyl)-butane,
2,6-di-(3-tert-butyl-5-methyl-2-hydroxybenzyl)-4-methylphenol,
1,1,3-tris-(5-tert-butyl-4-hydroxy-2-methylphenyl)-3-n-dodecyl-mercaptobutane,
ethylene glycol-bis[3,3-bis-(3'-tert-butyl-4'-hydroxyphenyl)-butyrate],
di-(3-tert-butyl-4-hydroxy-5-methylphenyl)-dicyclopentadiene, and
di-[2-(3'-tert-butyl-2'-hydroxy-5'-methyl-benzyl)-6-tert-butyl-4-methyl-phenyl]terephthalatate.

5. Benzyl compounds
1,3,5-tri-(3,5-di-tert-butyl-4-hydroxybenzyl)-2,4,6-trimethylbenzene,
di-(3,5-di-tert-butyl-4-hydroxybenzyl)sulfide,
3,5-di-tert-butyl-4-hydroxybenzyl-mercaptoacetic acid isooctyl ester,
bis-(4-tert-butyl-3-hydroxy-2,6-dimethylbenzyl)dithiolterephthalate,
1,3,5-tris-(3,5-di-tert-butyl-4-hydroxybenzyl)isocyanurate,
1,3,5-tris-(4-tert-butyl-3-hydroxy-2,6-dimethylbenzyl)isocyanurate,
3,5-di-tert-butyl-4-hydroxybenzyl-phosphonic acid dioctadecyl ester, and
calcium salt of 3,5-di-tert-butyl-4-hydroxybenzylphosphonic acid monoethyl ester.

6. Acylaminophenols
4-hydroxylauric acid anilide,
4-hydroxystearic acid anilide,
2,4-bisoctylmercapto-6-(3,5-di-tert-butyl-4-hydroxyanilino)-s-triazine, and
N-(3,5-di-tert-butyl-4-hydroxyphenyl)carbamic acid octyl ester.

7. Esters of β-(3,5-di-tert-butyl-4-hydroxyphenyl)-propionic acid with monohydric or polyhydric alcohols, for example with: methanol, octadecanol, 1,6-hexanediol, neopentyl glycol, thiodiethylene glycol, diethylene glycol, triethylene glycol, pentaerythritol, trishydroxyethyl isocyanurate or dihydroxyethyloxalic acid diamide.

8. Esters of β-(5-tert-butyl-4-hydroxy-3-methylphenyl)propionic acid with monohydric or polyhydric alcohols, for example with:
methanol, octadecanol, 1,6-hexanediol, neopentyl glycol, thiodiethylene glycol, diethylene glycol, triethylene glycol, pentaerythritol, trishydroxyethyl isocyanurate or dihydroxyethyloxalic acid diamide.

9. Amides of β-(3,5-di-tert-butyl-4-hydroxyphenyl)-propionic acid, for example:
N,N'-di-(3,5-di-tert-butyl-4-hydroxyphenylpropionyl)-hexamethylenediamine,
N,N'-di-(3,5-di-tert-butyl-4-hydroxyphenylpropionyl)-trimethylenediamine,
N,N'-di-(3,5-di-tert-butyl-4-hydroxyphenylpropionyl)-hydrazine.

10. Examples of amine antioxidants
N,N'-diisopropyl-p-phenylenediamine
N,N'-di-sec-butyl-p-phenylenediamine,
N,N'-bis(1,4-dimethylpentyl)-p-phenylenediamine,
N,N'-bis(1-ethyl-3-methylpentyl)-p-phenylenediamine,
N,N'-bis(-methylheptyl)-p-phenylenediamine,
N,N'-dicyclohexyl-p-phenylenediamine,
N,N'-diphenyl-p-phenylenediamine,
N,N'-di(naphthyl-2-)-p-phenylenediamine,
N-isopropyl-N'-phenyl-p-phenylenediamine, N-(1,3-dimethylbutyl)-N'-phenyl-p-phenylenediamine,
N-(1-methylheptyl)-N'-phenyl-p-phenylenediamine,
N-cyclohexyl-N'-phenyl-p-phenylenediamine,
4-(p-toluenesulfonamido)-diphenylamine,
N,N'-dimethyl-N,N'-di-sec-butyl-p-phenylenediamine, diphenylamine,
4-isopropoxydiphenylamine,
N-phenyl-1-naphthylamine,
N-phenyl-2-naphthylamine,
tert-octylated N-phenyl-1-naphthylamine,
octylated diphenylamine,
4-n-butylaminophenol,
4-butyrylaminophenol,
4-nonanoylaminophenol,
4-dodecanoylaminophenol,
4-octadecanoylaminophenol,
di-(4-methoxyphenyl)amine,
2,6-di-tert-butyl-4-dimethylaminomethylphenol,
2,4'-diaminodiphenylmethane,
4,4'-diaminodiphenylmethane,
N,N,N,N'-tetramethyl-4,4'-diaminodiphenylmethane,
1,2-di(phenylamino)ethane,
1,2-di-[(2-methylphenyl)-amino]ethane,
1,3-di(phenylamino)propane,
(o-tolyl)biguanide,
di-[4-(1',3'-dimethylbutyl)phenyl)amine, tert-octylated N-phenyl-1-naphthylamino, and mixture of mono- and dialkylated tert-butyl/tert-octyldiphenylamines.

Examples of metal passivators are:
for copper, for example: benzotriazole, tetrahydrobenzotriazole, 2-mercaptobenzotriazole, 2,5-dimercaptothiadiazole, salicylidene-propylenediamine and salts of salicylaminoguanidene.

Examples of rust inhibitors are:
(a) organic acids, the esters thereof, metal salts and anhydrides thereof, for example: N-oleylsarcosine, sorbitan monooleate, lead naphthenate, dodecenylsuccinic acid anhydride, alkenylsuccinic acid half-ester and 4-nonylphenoxyacetic acid;
(b) nitrogen-containing compounds, for example:
  I. primary, secondary or tertiary aliphatic or cycloaliphatic amines and amine salts of organic and inorganic acids, for example oil-soluble alkylammonium carboxylates;
  II. heterocyclic compounds, for example: substituted imidazolines and oxazolines;
(c) phosphorus-containing compounds, for example: amine salts of phosphoric acid partial esters;
(d) sulfur-containing compounds, for example: barium dinonylnaphthalenesulfonates and calcium petroleum sulfonates.

Examples of viscosity-index improvers are for example: polymethacrylate, vinyl pyrrolidone/methacrylate copolymers, polybutenes, olefin copolymers and styrene/acrylate copolymers.

Examples of pour-point depressors are for example: polymethacrylates and alkylated naphthalene derivatives.

Examples of dispersants/surfactants are for example: polybutenylsuccinimides, polybutenylphosphonic acid derivatives, basic magnesium, calcium and barium sulfonates and phenolates.

Examples of anti-wear additives are for example: compounds containing sulfur and/or phosphorus and/or halogen, such as sulfurised vegetable oils, zinc dialkyldithiophosphates, tritolylphosphate, chlorinates paraffins and alkyl- and aryldisulfides.

Furthermore, the aldosemercaptals of the formula I can also be used as additives for plastics and elastomers, wherein they are effective as thermostabilisers and antioxidants, for example for PVC, and, as adhesion promoters, especially for metal, glass, wood, ceramics and concrete. They also exhibit a good antistatic activity.

The aldosemercaptals of the formula I are added to the plastics at a concentration of 0.005 to 5% by weight, relative to the weight of the plastics material to be stabilised. There are preferably incorporated 0.05–2% by weight, and particularly 0.1 to 2% by weight, of the aldosemercaptals of the formula I, relative to the material to be stabilised.

Incorporation can be effected for example by mixing in the compounds of the formula I and optionally further additives by methods customarily used in practice, before or after moulding or shaping, or by applying the dissolved or dispersed compounds to the polymers, optionally with subsequent removal of the solvent by evaporation. The additives can be incorporated separately or as a mixture.

The aldosemercaptals of the formula I can be added also in the form of a masterbatch, which contains these compounds for example at a concentration of 2.5 to 25% by weight, to the plastics to be stabilised.

In the case of crosslinked polyethylene, the compositions according to the invention are added before crosslinking.

The materials thus stabilised can be used in the most varied forms, for example as sheets, particularly sheets for agricultural purposes, fibres, tapes, moulding compounds, profiles and foamed articles; or as binders for lacquers, adhesives or cements.

Examples of plastics which can be treated with the aldosemercaptals of the formula I are:
1. polymers of mono- and diolefins, for example polyethylene (which can be crosslinked), polypropylene, polyisobutylene, polybut-1-ene, polymethylpent-1-ene, polyisoprene or polybutadeine, and also polymers of cycloolefins, for example of cyclopentene and norbornene;
2. mixtures of the polymers mentioned under 1, for example mixtures of polypropylene with polyisobutylene;
3. copolymers of mono- and diolefins with each other or with other vinyl monomers, for example ethylene/propylene copolymers, propylene/but-1-ene copolymers, propylene/isobutylene copolymers, ethylene/but-1-ene copolymers, propylene/butadiene copolymers, isobutylene/isoprene copolymers, ethylene/alkylacrylate copolymers, ethylene/alkylmethacrylate copolymers, ethylene/vinyl acetate copolymers or ethylene/acrylic acid copolymers and salts thereof (ionomers), and also terpolymers of ethylene with propylene and a diene, such as hexadiene, dicyclopentadiene or ethylidene norbornene;
4. copolymers of styrene or α-methylstyrene with dienes or acrylic derivatives, for example styrene/butadiene, styrene/acrylonitrile, styrene/alkylmethacrylate, styrene/maleic anhydride, styrene/acrylonitrile/methyl acrylate; mixtures of high impact strength formed from styrene copolymers and another polymer, for example a polyacrylate, a diene polymer or an ethylene/propylene/diene terpolymer; and also block copolymers of styrene, for example styrene/butadiene/styrene, styrene/isoprene/styrene, styrene/ethylene-butylene/styrene or styrene-ethylene/propylene styrene;

5. graft copolymers of styrene, for example styrene with polybutadiene, styrene and acrylonitrile with polybutadiene, styrene and maleic anhydride with polybutadiene, styrene and alkyl acrylates or alkyl methacrylates with polybutadiene, styrene and acrylonitrile with ethylene-propylene-diene terpolymers, styrene and acrylonitrile with polyalkylacrylates or polyalkylmethacrylates, styrene and acrylonitrile with acrylate-butadiene copolymers, and mixtures thereof with the copolymers listed under 4, known for example as so-called ABS, MBS, ASA or AES polymers;

6. halogen-containing polymers, for example polychloroprene, chlorinated rubber, chlorinated or chlorosulfonated polyethylene, epichlorohydrin homo- and copolymers, especially polymers formed from halogen-containing vinyl com!pounds, for example: polyvinyl chloride, polyvinylidene chloride, polyvinyl fluoride or polyvinylidene fluoride, and also copolymers thereof, such as vinyl chloride/vinylidene chloride, vinyl chloride/vinyl acetate or vinylidene choride/vinyl acetate;

7. copolymers of monomers, such as $\alpha,\beta$-unsaturated acids and derivatives thereof with other unsaturated monomers, for example acrylonitrilebutadiene copolymers, acrylonitrile/alkyl acrylate copolymers, acrylonitrile/alkoxyalkyl acrylate copolymers, acrylonitrile/vinyl halide copolymers or acrylonitrile/alkyl methacrylate/butadiene terpolymers;

8. homo- and copolymers of cyclic ethers, such as polyalkylene glycols, polyethylene oxide or polypropylene oxide, or copolymers thereof with bis-glycidyl ethers;

9. polyurethanes which are derived on the one hand from polyethers, polyesters and polybutadienes containing hydroxyl end groups, and from aliphatic or aromatic polyisocyanates on the other hand, as well as precursors thereof;

10. natural polymers, such as cellulose, natural rubber or gelatine, and also chemically modified polymer-homologous derivatives thereof, such as cellulose acetates, cellulose propionates and cellulose butyrates, and cellulose ethers, such as methylcellulose;

11. mixtures (polyblends) of the aforementioned polymers, for example: PP/EPDM, polyamide 6/EPDM or ABS, PVC/EVA, PVC/ABS, PVC/MBS, PC/ABS or PBTP/ABS;

12. natural and synthetic organic substances, which are pure monomeric compounds or mixtures of such compounds, for example mineral oils, animal or vegetable fats, oils and waxes, or oils, waxes and fats based on synthetic esters (for example phthalates, adipates, phosphates or trimellithates), as well as mixtures of synthetic esters with mineral oils in any chosen weight ratio, such as are applied for example as spinning preparations, and also aqueous emulsions thereof; and 13. aqueous emulsions of natural or synthetic rubbers, for example natural rubber-latex or latices of carboxylated styrene/butadiene copolymers.

The aldoseeercaptals of the formula I can in practice be used together with other stabilisers. Examples of further additives, together with which the aldosemercaptals can be used, are as follows:

1. Antioxidants
1.1. Alkylated monophenols
2,6-di-tert-butyl-4-methylphenol,
2-tert-butyl-4,6-dimethylphenol,
2,6-di-tert-butyl-4-ethylphenol,
2,6-di-tert-butyl-4-n-butylphenol,
2,6-di-tert-butyl-4-i-butylphenol,
2,6-di-cyclopentyl-4-methylphenol,
2-($\alpha$-methylcyclohexyl)-4,6-dimethylphenol,
2,6-di-octadecyl-4-methylphenol,
2,4,6-tricyclohexylphenol, and
2,6-di-tert-butyl-4-methoxymethylphenol.

1.2 Alkylated hydroquinones
2,6-di-tert-butyl-4-methoxyphenol,
2,5-di-tert-butyl-hydroquinone,
2,5-di-tert-amyl-hydroquinone, and
2,6-diphenyl-4-octadecyloxyphenol.

1.3. Hydroxylated thiodiphenyl ethers
2,2'-thio-bis-(6-tert-butyl-4-methylphenol),
2,2'-thio-bis-(4-octylphenol),
4,4'-thio-bis-(6-tert-butyl-3-methylphenol), and
4,4'-thio-bis-(6-tert-butyl-2-methylphenol).

1.4. Alkylidene-bisphenols
2,2'-methylene-bis-(6-tert-butyl-4-methylphenol),
2,2'-methylene-bis-(6-tert-butyl-4-ethylphenol),
2,2'-methylene-bis-[4-methyl-6-($\alpha$-methylcyclohexyl)-phenol],
2,2'-methylene-bis-(4-methyl-6-cyclohexylphenol),
2,2'-methylene-bis-(6-nonyl-4-methylphenol),
2,2'-methylene-bis-(4,6-di-tert-butylphenol),
2,2'-ethylidene-bis-(4,6-di-tert-butylphenol),
2,2'-ethylidene-bis-(6-tert-butyl-4-isobutylphenol),
2,2'-methylene-bis-[6-($\alpha$-methylbenzyl)-4-nonylphenol],
2,2'-methylene-bis-6-($\alpha,\alpha$-dimethylbenzyl)-4-nonylphenol],
4,4'-methylene-bis-(2,6-di-tert-butylphenol),
4,4'-methylene-bis-(6-tert-butyl-2-methylphenol),
1,1-bis-(5-tert-butyl-4-hydroxy-2-methylphenyl)-butane,
2,6-di-(3-tert-butyl-5-methyl-2-hydroxybenzyl)-4-methylphenol,
1,1,3-tris-(5-tert-butyl-4-hydroxy-2-methylphenyl)-butane,
1,1-bis-(5-tert-butyl-4-hydroxy-2-methylphenyl)-3-n-dodecylmercaptobutane,
ethylene glycol-bis-[3,3-bis-(3'-tert-butyl-4'-hydroxyphenyl)-butyrate],
di-(3-tert-butyl-4-hydroxy-5-methylphenyl)-dicyclopentadiene, and
di-[2-(3'-tert-butyl-2'-hydroxy-5-methyl-benzyl)-6-tert-butyl-4-methyl-phenyl]-terephthalate.

1.5. Benzyl compounds
1,3,5-tri-(3,5-di-tert-butyl-4-hydroxybenzyl)-2,4,6-trimethylbenzene,
di-(3,5-di-tert-butyl-4-hydroxybenzyl)-sulfide,
3,5-di-tert-butyl-4-hydroxybenzyl-mercaptoacetic acid isooctyl ester,
bis-(4-tert-butyl-3-hydroxy-2,6-dimethylbenzyl)dithiol-terephthalete,
1,3,5-tris-(3,5-di-tert-butyl-4-hydroxybenzyl)-isocyanurate,
1,3,5-tris-(4-tert-butyl-3-hydroxy-2,6-dimethylbenzyl)isocyanurate,
3,5-di-tert-butyl-4-hydroxybenzylphosphonic acid dioctadecyl ester, and
calcium salt of 3,5-di-tert-butyl-4-hydroxybenzylphosphonic acid monoethyl ester.

1.6. Acylaminophenols
4-hydroxylauric acid anilide,
4-hydroxystearic acid anilide,
2,4-bis-octylmercapto-6-(3,5-di-tert-butyl-4-hydroxyanilino)-s-triazine, and N-(3,5-di-tert-butyl-4-hydroxyphenyl)-carbamic acid octyl ester.

1.7. Esters of β-(3,5-di-tert-butyl-4-hydroxyphenyl)-propionic acid with monohydric or polyhydric alcohols, for example with:
methanol, octadecanol, 1,6-hexanediol, neopentyl glycol, thiodiethylene glycol, diethylene glycol, triethylene glycol, pentaerythritol, tris-hydroxyethyl isocyanurate, and
di-hydroxyethyloxalic acid diamide.

1.8. Esters of β-(5-tert-butyl-4-hydroxy-3-methylphenyl) propionic acid with monohydric or polyhydric alcohols, for example with:
methanol, octadecanol, 1,6-hexanediol, neopentyl glycol, thiodiethylene glycol, diethylene glycol, triethylene glycol, pentaerythritol, tris-hydroxyethyl isocyanurate, and di-hydroxyethyloxalic acid diamide.

1.9. Amides of β-(3,5-di-tert-butyl-4-hydroxyphenyl) propionic acid for example:
N,N'-di-(3,5-di-tert-butyl-4-hydroxyphenylpropionyl)-hexamethylenediamine,
N,N'-di-(3,5-di-tert-butyl-4-hydroxyphenylpropionyl)-trimethylenediamine, and
N,N'-di-(3,5-di-tert-butyl-4-hydroxyphenylpropionyl)-hydrazine.

2. UV absorbers and light stabilisers 2.1. 2-(2'-Hydroxyphenyl)-benzotriazoles, for example: the 5'-methyl-, 3',5'-di-tert-butyl-, 5'-tert-butyl-, 5'-(1,1,3,3-tetramethylbutyl)-, 5-chloro-3',5'-di-tertbutyl-, 5-chloro-3'-tert-butyl-5-methyl-, 3'-sec-butyl-5'-tert-butyl-, 4'-octoxy-, 3',5'-di-tert-amyl- and 3',5'-bis-(α,α-dimethylbenzyl) derivative.

2.2. 2-Hydroxybenzophenones, for example: the 4-hydroxy-, 4-methoxy-, 4-octoxy-, 4-decyloxy-, 4-dodecyloxy-, 4-benzyloxy-, 4,2',4'-trihydroxy- and 2'-hydroxy-4,4'-dimethoxyderivative.

2.3. Esters of unsubstituted or substituted benzoic acids, for example: 4-tert-butyl-phenyl salicylate, phenyl salicylate, octylphenyl salicylate, dibenzoylresorcinol, bis-(4-tert-butylbenzoyl)resorcinol, benzoylresorcinol, 3,5-di-tert-butyl-4-hydroxybenzoic acid-2,4-di-tert-butylphenyl ester and 3,5-di-tert-butyl-4-hydroxybenzoic acid hexadecyl ester.

2.4. Acrylates, for example: α-cyano-β,β-diphenylacrylic acid ethyl ester or -isooctyl ester, α-carbomethoxycinnamic acid methyl ester, α-cyano-β-methyl-p-methoxycinnamic acid methyl ester or -butyl ester, α-carbomethoxy-p-methoxycinnamic acid methyl ester and N-(β-carbomethoxy-β-cyanovinyl)-2-methyl-indoline.

2.5. Nickel compounds, for example: nickel complexes of 2,2'-thio-bis-4-(1,1,3,3tetramethylbutyl)-phenol], such as the 1:1 or 1:2 complex, with or without additional ligands, such as n-butylamine, triethanolamine or N-cyclohexyl-diethanolamine, nickel dibutyl-dithiocarbamate, nickel salts of 4-hydroxy-3,5 di-tert-butylbenzylphosphonic acid monoalkyl esters, such as of the methyl of ethyl ester, nickel complexes of ketoximes, such as of 2-hydroxy-4-methyl-phenyl undecyl ketonoxime, and nickel complexes of 1-phenyl-4-lauroyl-5-hydroxypyrazole, with or without additional ligands.

2.6. Sterically hindered amines, for example: bis-(2,2,6,6-tetramethylpiperidyl)-sebacate, bis-(1,2,2,6,6,-pentamethylpiperidyl)-sebacate, n-butyl-3,5-di-tert-butyl-4-hydroxybenzylmalonic acid-bis-(1,2,2,6,6-pentamethylpiperidyl) ester, condensation product of 1-hydroxyethyl-2,2,6,6-tetramethyl-4-hydroxypiperidine and succinic acid, condensation product of N,N'-(2,2,6,6-tetramethylpiperidyl)hexamethylenediamine and 4-tert-octylamino-2,6-dichloro-1,3,5-s-triazine, tris-(2,2,6,6-tetramethylpiperidyl)nitrilotriacetate, tetrakis-(2,2,6,6-tetramethyl-4-piperidyl)-1,2,3,4-butanetetracarboxylic acid, and 1,1'-(1,2-ethanediyl)-bis-(3,3,5,5-tetramethylpiperazinone).

2.7. Oxalic acid diamides, for example: 4,4'-dioctyloxyoxanilide, 2,2'-di-octyloxy-5,5'-di-tert-butyloxanilide, 2,2'-di-dodecyloxy-5,5'-di-tert-butyl-oxanilide, 2-ethoxy-2'-ethyl-oxanilide, N,N''-bis-(3-dimethylaminopropyl)oxalamide, 2-ethoxy-5-tert-butyl-2'-ethyloxanilide and its mixtures with 2-ethoxy-2'-ethyl-5,4'-di-tert-butyloxanilide and mixtures of ortho- and para-methoxy-disubstituted oxanilidenes and mixtures of o- and p-ethoxy-disubstituted oxanilidenes.

3. Metal deactivators, for example: N,N'-diphenyloxalic acid diamide, N-salicylal-N'-salicyloylhydrazine, N,N'-bissalicyloylhydrazine, N,N'-bis-(3,5-di-tert-butyl-4-hydroxyphenylpropionyl)-hydrazine, 3-salicyloylamino-1,2,4-triazole and bis-benzylideneoxalic acid dihydrazide.

4. Phosphites and phosphonites, for example: triphenylphosphite, diphenylalkyl phosphites, phenyldialkyl phosphites, tri-(nonylphenyl) phosphite, trilauryl phosphite, trioctadecyl phosphite, distearyl-pentaerythritol diphosphite, tris-(2,4-di-tert-butylphenyl) phosphite, diisodecylpentaerythritol diphosphite, di-(2,4-di-tert-butylphenyl)-pentaerythritol diphosphite, tris-tearylsorbitol triphosphite and tetrakis-(2,4-di-tert-butylphenyl)-4,4'-biphenylene diphosphonite.

5. Peroxide scavengers, for example: esters of β-thiodipropionic acid, for example the lauryl, stearyl, myristyl or tridecyl ester, mercaptobenzimidazole, the zinc salt of 2-mercaptobenzimidazole, zinc-dibutyl-dithiocarbamate, dioctadecyldisulfide and pentaerythritol-tetrakis-(β-dodecylmercapto)propionate.

6. Polyamide stabilisers, for example: copper salts in combination with iodides and/or phosphorus compounds and salts of divalent manganese.

7. Basic co-stabilisers, for example: melamine, polyvinylpyrrolidone, dicyandiamide, triallyl cyanurate, urea derivatives, hydrazine derivatives, amines, polyamides, polyurethanes, alkali metal salts and alkaline-earth metal salts of higher fatty acids, for example calcium stearate, zinc stearate, magnesium stearate, sodium ricinoleate and potassium palmitate, antimony pyrocatechoate or tin pyrocatechoate.

8. Nucleating agents, for example: 4-tert-butylbenzoic acid, adipic acid and diphenylacetic acid.

9. Fillers and reinforcing agents, for example: calcium carbonate, silicates, glass fibres, asbestos, talcum, kaolin, mica, barium sulfate, metal oxides and metal hydroxides, carbon black and graphite.

10. Other additives, for example: placticisers, lubricants, emulsifiers, pigments, optical brighteners, flameproofing agents, antistatic agents and blowing agents.

The aldosemercaptals of the formula I are suitable as additives for mineral and synthetic lubricating oils, hydraulic fluids which can be based on oil or water or on mixtures thereof, and lubricating greases. They can be used as multipurpose additives, and act in particular against corrosion and oxidation; they moreover improve the high-pressure protection, wear protection and dispersing properties and, as adhesion promoters, they prevent dripping and spattering of oil.

The following Examples further illustrate the production of the aldosemercaptals of this invention.

General Example A

The double molar amount of a mercaptan is added to an aldose, and trifluoroacetic acid is subsequently added in an amount sufficient to obtain a 50% solution. The clear solution is allowed to stand at room temperature, and the course of the reaction is verified by SH determinations. After the SH has finished decreasing, processing can be carried out by the following three methods: $A_1$, $A_2$ and $A_3$.

$A_1$ The reaction product is precipitated with water, the solid substance is filtered off with suction and repeatedly washed with water. The residue is then recrystallised from the respective organic solvent.

$A_2$ Diethyl ether is added to the reaction mixture; water are formed; the is subsequently added until two phases aqueous phase is then separated, and the organic phase treated with an aqueous sodium bicarbonate solution. After drying over sodium sulfate and filtration until clear, the solvent is distilled off in a rotary evaporator, and the residue is recrystallised from the organic solvent concerned.

$A_3$ The trifluoroacetic acid is distilled off in a rotary evaporator, and the residue is recrystallised from the respective organic solvent.

EXAMPLE 1: 1st Version 36 parts by weight of D-(+) glucose, 31 parts by weight of 2-mercaptoethanol, 16 parts by weight of LEWASORB AC 10/H and 30 parts by weight of water are stirred for 8 to 12 hours at 45°–50° C. The course of the reaction is verified by SH determinations. After the reaction has finished, 100 parts by weight of $H_2O$ are added to the mixture; the resin is then separated by filtration, washed with 100 parts by weight of water, and the combined filtrates are concentrated in the rotary evaporator. The 57.8 g of residue are recrystallised from 150 ml of ethanol.

Yield: 28.3 parts by weight, 45% of the theoretical yield; white crystals, m.p. 84°–86° C.

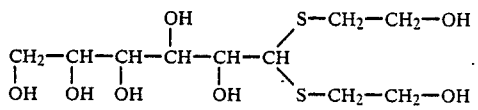

EXAMPLE 1: 2nd Version

A mixture of 200 g of D-(+) glucose, 156 g of 2-mercaptoethanol, 120 g of LEWASORB AC 10/H and 150 g of methanol are heated, with stirring, at 45°–50° C. for 6–12 hours. After completion of the reaction, 400 ml of methanol are added to the reaction mixture; vigorous stirring is maintained for 10 minutes and, after precipitation of the solid material, the supernatant solution is decanted. This operation is repeated with 200 ml of methanol. The combined methanolic solutions are concentrated in a rotary evaporator, and the unreacted 2-mercaptoethanol is distilled off by means of an oil pump.

Yield: 294 g  92% of the theoretical yield.

On account of its low crystallisation tendency, this compound is advantageously prepared as an approximately 50% solution in water.

Using the catalyst remaining in the reaction vessel, it is possible to repeatedly perform the reaction in the manner described in the foregoing and with the same yield.

EXAMPLES 2–14

By a process analogous to that described in the general Example A, there are produced further compounds (Examples 2–6 and 8–14) which, in addition to Example 1, are summarised in the following Table 1.

TABLE 1

| Example No. | Formula | Analytical data melting point [°C.] | Produced according to Example | Observations: x% of the theoretical yield/ (recrystallised from y)/further properties |
|---|---|---|---|---|
| 1 | $CH_2$—CH—CH—CH—CH—CH(OH)(S—$CH_2$—$CH_2$—OH)$_2$ with OH, OH, OH, OH substituents | 86 |  | 45%/(ethanol) |
| 2 | $CH_2$—CH—CH—CH—CH—CH with OH, OH, OH, OH, OH and cyclic S—S (dithiolane) | 143 | $A_3$ | 52%/(methanol) |
| 3 | $CH_2$—CH—CH—CH—CH(—S—Ph)$_2$ with OH, OH, OH, OH | 153 | $A_2$ | 30%/(i-propanol) |
| 4 | $CH_2$—CH—CH—CH—CH(—S—$CH_2$—Ph)$_2$ with OH, OH, OH, OH | 134 | $A_1$ | 73%/(i-propanol) |
| 5 | $CH_2$—CH—CH—CH—CH(—S—$^nC_8H_{17}$)$_2$ with OH, OH, OH, OH | 112 | $A_1$ | 65% (i-propanol) (soluble in oil at 70° C.) |

TABLE 1-continued

| Example No. | Formula | Analytical data melting point [°C.] | Produced according to Example | Observations: x% of the theoretical yield/ (recrystallised from y)/further properties |
|---|---|---|---|---|
| 6 | $CH_2-CH-CH-CH-CH-CH(-S-^nC_8H_{17})_2$ with OH groups on C1, C2, C3, C4, C5 | wax/gel | $A_2$ | 91% (soluble in oil at RT)* |
| 7 | $CH_2-CH-CH-CH-CH-CH(-S-C_2H_5)_2$ with OH on C1, C2, C3, C5 | 128 | commercially available (or accord. to $A_3$) | — |
| 8 | $CH_2-CH-CH-CH-CH-CH(-S-^nC_{12}H_{25})_2$ with OH on C1, C2, C3, C5 | 125 | $A_1$ | 89%/(i-propanol) |
| 9 | $CH_2-CH-CH-CH-CH-CH(-S-^nC_{12}H_{25})_2$ with OH on C1, C2, C3, C4, C5 | 143 | $A_1$ | 56%/(i-propanol) |
| 10 | $CH_2-CH-CH-CH-CH-CH(-S-^nC_{12}H_{25})_2$ with OH on C1, C2, C3, C5 | 131 | $A_1$ | 64%/(i-propanol) |
| 11 | $CH_2-CH-CH-CH-CH-CH(-S-^nC_{12}H_{25})_2$ with OH on C1, C2, C3, C5 | 100 | $A_1$ | 63%/(i-propanol) |
| 12 | $CH_2-CH-CH-CH-CH(-S-^nC_{12}H_{25})_2$ with OH on C1, C2, C3, C4 | 101 | $A_1$ | 69%/(i-propanol) |
| 13 | $CH_2-CH-CH-CH-CH(-S-^nC_{12}H_{25})_2$ with OH on C2, C3, C4, C5 | 96 | $A_2$ | 43%/(ethyl acetate)/(soluble in oil at 60° C.) |
| 14 | $CH_2-CH-CH-CH-CH(-S-^nC_{12}H_{25})_2$ with OH on C1, C2, C4 | 87 | $A_2$ | 56%/(i-propanol)/ (soluble in oil at 50° C.) |
| 15 | $CH_2-CH-CH-CH-CH-CH(-S-CH_2-CH-CH_2-C(-CH_3)_2)$ with OH on C1,C2,C3,C5 and CH$_3$ on branched carbons | 130–32 | $A_2$ | 43%/(i-propanol) |

*RT = room temperature

The following application Examples serve to further illustrate the results obtained by applying in practice the materials containing additives according to the invention: application Examples Nos. 1–3 relate to lubricants and application Example No. 4 to plastics.

Application Example 1:

With the Shell four-ball apparatus (IP 239/73 - Extreme pressure and wear lubricant test for oils and greases four-ball machine), the following values are obtained:
1. W.L. = Weld Load: this is the load under which the 4 balls weld together within 10 seconds.
2. W.S.D. = Wear Scar Diameter in mm.: this is the mean wear diameter with a load of 400 N during 10 minutes.

There is used as test fluid for testing the effectiveness of the additives (Examples Nos. 2 and 7) deionised water containing, as rust inhibitor, 0.75 % by weight of 2,4,6-tris-(5'-carboxypentylamino)-1,3,5-triazine, and triethanolamine in an amount sufficient to obtain a pH value of 8.5. As the test fluid for the effectiveness of the additive (Example No. 1), there is used only deionised water, the pH value being 9.4.

TABLE 2

| | 2.5% of additive in the test fluid Test with the Shell four-ball apparatus | |
|---|---|---|
| Additive: Example No. | W.L. (N) | W.S.D. 10 min. (mm) |
| 1 | 2250 | 0,75 |
| 2 | 1700 | 0,7 |

TABLE 2-continued

|   | 2.5% of additive in the test fluid Test with the Shell four-ball apparatus | |
|---|---|---|
| Additive: Example No. | W.L. (N) | W.S.D. 10 min. (mm) |
| 7 | 1450 | 1,05 |

Application Example 2:

The area of wear is determined with the wear tester according to Reichert (Reichert Wear Test DBGM 1749247).

In this wear tester, a rigidly clamped cylinder is pressed, by way of a double lever system, against a rotating sliding ring, the lower third of this being immersed in the test fluid, the anti-wear activity of which is to be determined. When the ring is rotating, there are formed, depending on the anti-wear activity of the fluid on the cylinder, areas of wear, and the extent of these will depend on the load capacity of the test fluid.

Test conditions for the apparatus:

| | |
|---|---|
| amount of fluid: | about 25 ml |
| test components: | ring and roller, axes crossed, |
| sliding rate: | 1.70 m/sec |
| duration of test: | ≙ 100 meters distance traversed |
| ring and roller material: | steel, hardened |
| normal load: | 15 N loading weight |
| type of friction: | sliding friction |
| quantity to be measured: | area of wear in mm² |

There is used as test fluid for testing the effectiveness of the additives (Examples Nos. 2 and 7) deionised water containing, as rust inhibitor, 0.75 % by weight of 2,4,6-tris-(5'-carboxypentylamino)-1,3,5-triazine, and triethanolamine in an amount sufficient to obtain a pH value of 8.5. As the test fluid for the effectiveness of the additive (Example No. 1) there is used only deionised water, the pH value being 9.4.

In order to show the activity of the test fluid, there is given here, as a comparison, the value obtained in the Reichert Test for a reference fluid consisting of 50% of deionised water and 50% of ethanol: this value is within the range of 28 to 30 mm².

TABLE 3

| Concentration Additive Example No. | 2.5% of additive in the test fluid | | | Test fluid without additive |
|---|---|---|---|---|
| | 1 | 2 | 7 | |
| Reichert Wear Test (mm²) | 15,0 | 8,7 | 11,7 | 28 |
| | 14,5 | 8,7 | 13,2 | 28 |
| | 14,3 | 8,0 | 13,2 | 30 |

Application Example 3

The corrosion properties are determined by the "shavings filter paper method" according to DIN 51360/Part 2.

With this method, a mixture containing, inter alia, also the additive to be tested is prepared in a beaker with water, in accordance with specific instructions. Grey-iron shavings on a round filter are wetted with the freshly prepared mixture; they are then exposed in a Petri dish to room temperature for 2 hours, and the round filter is subsequently visually examined for signs of corrosion.

The degree of corrosion is evaluated on the basis of a Table (cf. DIN 51360/Part 2), in which 0 signifies no corrosion and 1, 2, 3 and 4 denote increasing severity of corrosion.

There is used as test fluid for testing the effectiveness of the additives (Examples Nos. 2 and 7) deionised water containing, as rust inhibitor, 0.75 % by weight of 2,4,6-tris-(5'-carboxypentylamino)-1,3,5-triazine, and triethanolamine in an amount sufficient to obtain a pH value of 8.5. As the test fluid for determining the acitvity of the additive (Example No. 1), there is used only deionised water, the pH value being 9.4.

TABLE 4

| Concentration | 2.5% of additive in the test fluid | | |
|---|---|---|---|
| additive Example No. | 1 | 2 | 7 |
| corrosion | 0 | 0 | 0 |

Application Example 4: Static heat test

In order to test the thermostabilising action of specific additives, there is used a process in which the change in colour of test sheets at constant elevated temperature is assessed as a function of time.

The test sheets are produced according to the following formulation:

| | |
|---|---|
| SOLVIC 246 GA | 100.00 parts |
| REOPLAST 39 | 3.00 parts |
| calcium stearate | 0.35 part |
| zinc stearate | 0.15 part |
| IRGASTAB CH 300 | 0.55 part |
| test substance | X parts = 2.5 mmols. |

The test sheets are produced on a roll mill at 180° C., the sheet material having a thickness of 0.3 mm.

Sections of sheet of the same dimensions are then kept in a heating chamber at constant temperature (180° C.). After fixed intervals of time (cf. Table 5), a specimen is taken to assess the change in colour. The test is continued until a distinct change to darker shades of colour has occurred. It is thus possible by an optical comparison to draw conclusions with respect to the effectiveness of the stabilisers.

The optical comparison is effected by measurement of the Yellowness Index according to DIN 6167 (ASTM D 1925-70).

TABLE 5

| Test substance Ex. No. (cf. Table 1) | x parts of test substance in the test sheet | Yellowness-Index determination | | | | | | | | | |
|---|---|---|---|---|---|---|---|---|---|---|---|
| | | Test sheet without test substance | Test sheet with test substance after y minutes | | | | | | | | |
| | | | 0 min | 5 min | 10 min | 15 min | 20 min | 25 min | 30 min | 35 min | 40 min | 45 min |
| 2 | 0.64(≙2.5 mmol) | 25.8 | 10.5 | 16.1 | 20.8 | 24.9 | 38.6 | 56.3 | 90.1 | 96.9 | 117.0 | 124.3 |
| 3 | 0.96(≙2.5 mmol) | 23.9 | 9.4 | 12.7 | 16.0 | 20.2 | 19.6 | 28.8 | 36.3 | 42.3 | 58.1 | 90.0 |
| 6 | 1.14(≙2.5 mmol) | 18.0 | 12.0 | 16.7 | 22.3 | 25.6 | 28.2 | 34.1 | 35.9 | 50.9 | 48.4 | 81.7 |

What is claimed is:

1. A lubricant containing 0.001 to 5.070, by weight, a compound of the formula (I)

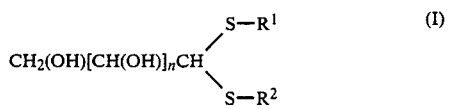

wherein n is an integer from 2 to 6, and wherein $R^1$ and $R^2$ are identical or different, and in each case are $C_1$-$C_{18}$-alkyl, which is unsubstituted, substituted or interrupted by —O— or —S—, or are —($CH_2$)$_r$—CO—N($C_1$-$C_{17}$-alkyl)$_2$, r being 1 or 2, or are phenyl, benzyl or —($CH_2$)$_r$—CO—O—$R^3$, in which r can be 1 or 2 and $R^3$ is an alkali metal or $C_1$-$C_{14}$-alkyl; also wherein $R^1$ and $R^2$ are —$CH_2$—CH(OH)—R, in which $R^4$ is hydrogen, or $C_1$-$C_{16}$-alkyl, unsubstituted or substituted by —OH, or —$CH_2$—Y—($C_1$-$C_{15}$-alkyl), in which Y is —O— or —S—; or wherein $R^1$ and $R^2$ together form —($CH_2$'-$_{hydroxy-m}$—, in which m is an integer from 2 to 4.

2. A lubricant according to claim 1, which contains a compound of the formula (I) wherein n is an integer from 3 to 6, and wherein $R^1$ and $R^2$ are identical and are $C_1$-$C_{16}$-alkyl, which is unsubstituted or interrupted by —O— or —S—, or are phenyl, benzyl or —$R^4$ in which ($CH_2$)$_r$—CO—O—$R^3$, in which r can be 1 or 2 and $R^3$ is an alkali metal; or wherein $R^1$ and $R^2$ are —$CH_2$—(OH)—$R^4$ in which hydrogen or $C_1$-$C_{14}$-alkyl or —$CH_2$—O—($C_1$-$C_{13}$-alkyl); or wherein $R^1$ and $R^2$ together form —($CH_2$·$_m$—, in which m is an integer from 2 to 4.

3. A lubricant according to claim 2, which contains a compound of the formula (I) wherein n is an integer from 3 to 6, and wherein $R^1$ and $R^2$ are identical and are $C_8$-$C_{16}$-alkyl or —$CH_2$—O—($C_7$-$C_{15}$-alkyl), phenyl, benzyl or —$CH_2$—COOK, —$CH_2$—COONa or —$CH_2$—$CH_2$—COOK; or wherein $R^1$ and $R^2$ are —$CH_2$—CH(OH)—$R^4$, which $R^4$ is hydrogen or $C_6$-$C_{14}$-alkyl or —$CH_2$—O—($C_5$-$C_{13}$-alkyl); or wherein $R^1$ and $R^2$ together form —($CH_2$)$_m$—, in which m is an integer from 2 to 4.

4. A compound of the formula (I)

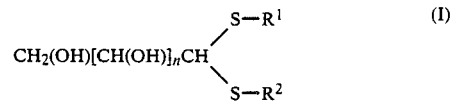

wherein n is an integer from 2 -o 6, and wherein $R^1$ and $R^2$ are identical or different and in each case are —($CH_2$)$_r$—CO—O—$R^3$, in which r is 1 or 2, and $R^3$ is an alkali metal or $C_1$-$C_{14}$-alkyl or are —$CH_2$—CH(OH)—$R^4$, in which $R^4$ is hydrogen, or $C_1$-$C_{16}$-alkyl, unsubstituted or substituted by —OH, or is —$CH_2$—Y—($C_1$-$C_{15}$-alkyl), in which Y is —O— or —S—.

5. A compound according to claim 4, wherein n is an integer from 3 to 6, and wherein $R^1$ and $R^2$ are identical, and are q can be 1 to 5, —$CH_2$—CH(OH)—$R^4$, in which $R^4$ is hydrogen or $C_1$-$C_{14}$-alkyl or —$CH_2$—O—($C_1$-$C_{13}$-alkyl).

6. A compound according to claim 5 wherein n is an integer from 4 to 6, and wherein $R^1$ and $R^2$ are identical and are -2-ethyl-hexyl, -2-butyl-octyl, -2-hexyl-decyl, —$CH_2$—COOK, —$CH_2$—COONa or —$CH_2$—$CH_2$—COOK; or wherein $R^1$ and $R^2$ are —$CH_2$—CH(OH)—$R^4$, in which $R^4$ is hydrogen, or $C_6$-$C_{14}$-alkyl or —$CH_2$—O—($C_5$-$C_{13}$-alkyl).

7. A method for stabilizing a lubricant, which comprises incorporating into said lubricant a compound of the formula (I) according to claim 1 in an amount of from 0.001 to 5%, by weight.

* * * * *